(12) United States Patent  
Baer

(10) Patent No.: US 9,188,784 B2  
(45) Date of Patent: *Nov. 17, 2015

(54) FORMING LIGHT BEAMS AND PATTERNS WITH ZERO INTENSITY CENTRAL POINTS

(71) Applicant: Stephen C Baer, Cambridge, MA (US)

(72) Inventor: Stephen C Baer, Cambridge, MA (US)

( * ) Notice: Subject to any disclaimer, the term of this patent is extended or adjusted under 35 U.S.C. 154(b) by 16 days.

This patent is subject to a terminal disclaimer.

(21) Appl. No.: 13/783,323

(22) Filed: Mar. 3, 2013

(65) Prior Publication Data

US 2013/0201558 A1    Aug. 8, 2013

Related U.S. Application Data

(63) Continuation of application No. 12/526,149, filed as application No. PCT/US2008/053349 on Feb. 7, 2008, now Pat. No. 8,390,928.

(60) Provisional application No. 60/888,764, filed on Feb. 7, 2007, provisional application No. 60/891,046, filed on Feb. 22, 2007.

(51) Int. Cl.
```
G02B 5/30      (2006.01)
G02B 27/09     (2006.01)
G02B 21/00     (2006.01)
```
(52) U.S. Cl.
CPC ........ *G02B 27/0927* (2013.01); *G02B 27/0988* (2013.01); *G02B 21/0032* (2013.01)

(58) Field of Classification Search
USPC ............ 359/489.01, 489.05, 489.07, 489.08, 359/489.15, 489.19, 580, 583
See application file for complete search history.

(56) References Cited

PUBLICATIONS

List of References cited by applicant and considered by examiner filed Feb. 8, 2013 in parent U.S. Appl. No. 12/526,149.*
List of References cited by applicant and considered by examiner filed Dec. 7, 2011 in parent U.S. Appl. No. 12/526,149.*
List of References filed Dec. 7, 2011 in parent U.S. Appl. No. 12/526,149.*

\* cited by examiner

*Primary Examiner* — Frank Font

(57) ABSTRACT

In order to produce a beam with a zero intensity axial ray or to produce a beam that when focused will produce an image of a doughnut shaped pattern with a zero intensity central point, a beam with a uniform or Gaussian profile is directed to a plurality of transparent plates, arranged in pairs on opposite sides of the beam axis, such that for at least one pair, the plates have a composition and thickness different from each other, and chosen so that the transmitted light has a phase difference of half a wavelength for at least three different wavelengths. An additional plate with a center on the perpendicular of the line connecting the first two plates has a composition and thickness such that the light transmitted through that additional plate has a phase difference of a quarter wavelength with respect to the light transmitted through one of the plates of said first pair of plates, at least one wavelength.

15 Claims, 6 Drawing Sheets

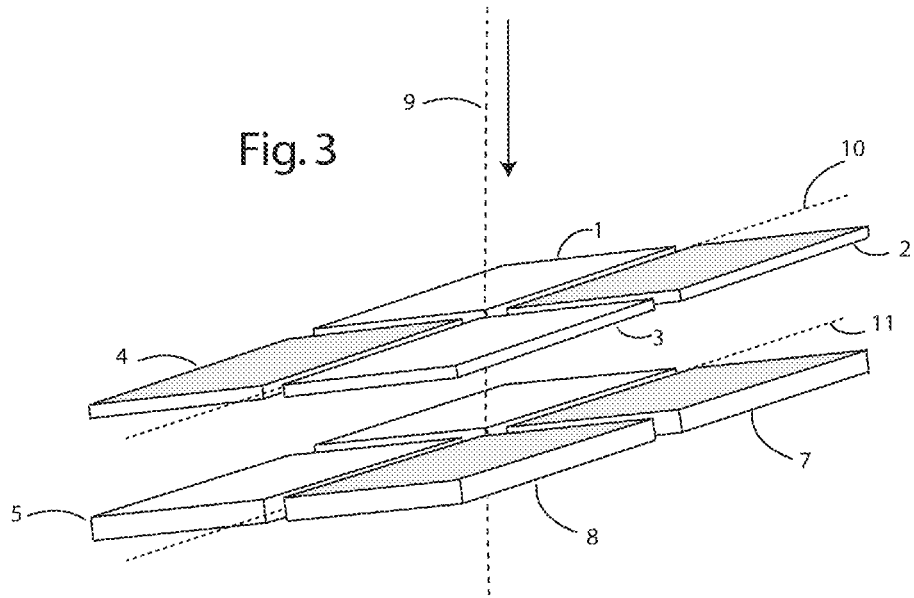
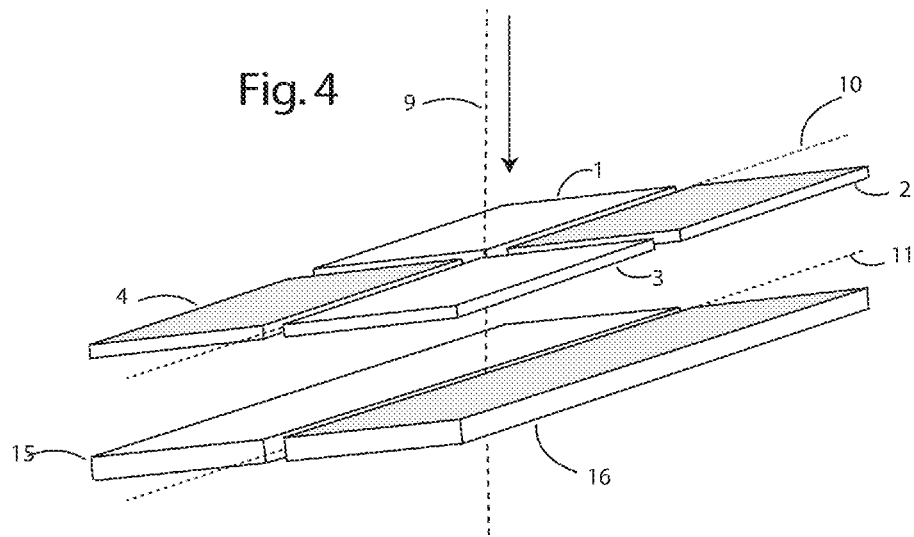

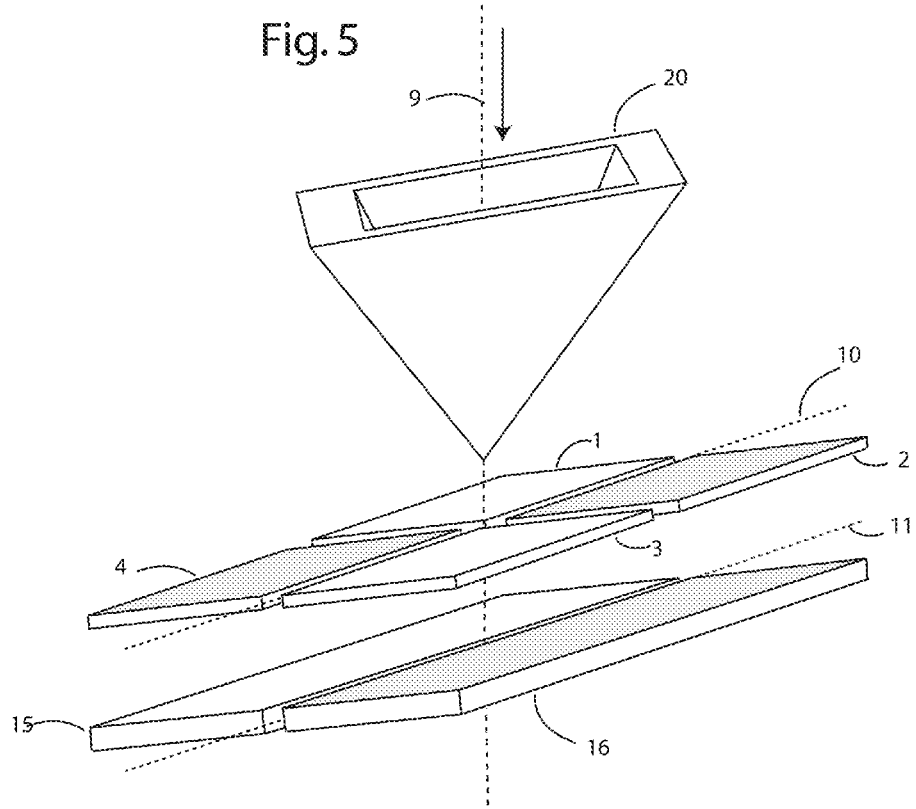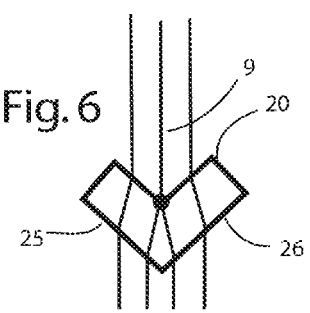

FORMING LIGHT BEAMS AND PATTERNS WITH ZERO INTENSITY CENTRAL POINTS

CROSS REFERENCE TO RELATED APPLICATIONS

This application is a continuation of U.S. patent application Ser. No. 12/526,149, now U.S. Pat. No. 8,390,928, which claims priority from U.S. Provisional Patent Application Ser. No. 60/888,764, filed Feb. 7, 2007 and from U.S. Provisional Patent Application Ser. No. 60/891,046, filed Feb. 22, 2007, the entire disclosures of which are hereby incorporated by reference.

FIELD OF THE INVENTION

The present invention relates to optical devices, and more particularly, devices for modifying the profile of a propagating beam. Still more particularly the present invention relates to devices that create beams either having a substantially zero intensity on their propagation axis and/or that when focused have a substantially zero intensity at a central point in the plane of focus.

BACKGROUND OF THE INVENTION

In the STED microscope (Hell and Wichmann U.S. Pat. No. 5,731,588, Baer, U.S. Pat. No. 5,866,911), the resolution of a scanning fluorescent microscope is improved by scanning the spot of excitation light synchronously and concentrically with a doughnut-shaped beam of a wavelength able to quench the fluorescent excitation by stimulated emission. Because near the center of the doughnut-shaped beam, the intensity increases with distance from the center, the quenching also increases with such distance, selectively quenching the periphery of the scanned spot, decreasing its size and thereby increasing the resolution of the microscope. In the form of STED microscope in which the doughnut-shaped beam has a central point of substantially zero intensity (Baer U.S. Pat. No. 5,866,911), by increasing the power of that beam, the quenching can reach any desired level at arbitrary closeness to the central point, without quenching fluorescence at the central point. This leads to resolution limited effectively only by the ability to generate the high powers of the doughnut-shaped beam and the ability of the specimen to tolerate the high powers. Since that first proposed use of a zero-centered doughnut-shaped beam in microscopy, several other microscopy techniques have been proposed using such beams.

Because in microscopy applications of such beams, the optimum wavelength of the quenching beam depends on the fluorescent dye or protein, it is desirable to have a method for forming such beams where the wavelength can be changed, sometimes very rapidly, while preserving the zero-intensity of the beam central point. Also, it is sometimes desirable to make such doughnut shaped beams with light of very short pulses that have a relatively broad spectral distribution. Finally, to improve the quality of the doughnut beam produced, it may be desirable to locate the doughnut beam making means as close as possible to the microscope objective lens as possible, in which case the fluorescent light emitted from the specimen would have to pass through said means in addition to both the excitation and quenching beams, and each of these bands of light would in general have different wavelengths. Therefore, ideally, the method for making the zero-centered doughnut-shaped beams would be invariant with respect to the wavelength.

Several methods have been proposed to address the problem of making zero-centered doughnut beams that can operate at more than one wavelength. Baer (PCT #US06/01959) proposed creating the doughnut pattern by means of a pyramid of glass triangles, in conjunction with a four-quadrant reflector. By adjusting the various phase retardations by tilting of the pyramid and translation of the reflective quadrants, the device can be corrected for two chosen wavelengths, and is approximately correct for the wavelengths between these two. However, because in this application, phase errors of even a small fraction of a wavelength can be detrimental to the performance of the system, such correction is not always adequate, particularly over a large wavelength range.

Another proposed solution has been to use an electronically programmable Spatial Light Modulator "SLM" (Hamamatsu Photonics K.K.) which can be reprogrammed as the wavelength is changed. However this proposed solution involves introducing additional optics to direct the beam onto the SLM and pass the reflected beam to the rest of the system, and in some cases to expand the beam for presentation to the SLM and to contract it for presentation to the rest of the optical system, and such optics create an opportunity for scattering, spurious reflection and introduction of additional phase errors. Furthermore the system is relatively expensive, and cannot deal with extremely rapid changes in wavelength required in some microscope techniques or creation of zero-center patterns from an intrinsically broadband source.

Yet another solution has been to create a plurality of spiral phase plates on a common glass sheet backing, such that each separate phase plate is corrected for a specific wavelength, and the wavelengths for the individual plates differed by 20 nm, covering a chosen interval of the spectrum. However even when a given phase plate is used with the exact wavelength for which it had been designed, it is difficult to control the thickness of the think layer coatings with sufficient accuracy to create a perfect pattern with a substantially zero intensity center. Also it is impossible to quickly vary excitation wavelength because of the need to rotate the glass sheet to put another phase plate into position. Furthermore the system cannot work with a broadband source.

Finally, Gugel (U.S. Patent Appl 2006/0007535 A1) has proposed using the relative wavelength independent phase shift during total internal reflection, combined with the difference in phase shift depending on whether or not there is a metallic backing layer overlying the reflecting surface, to approximate an achromatic phase shift, between a beam portion reflected from a surface with a metallic backing layer compared to a beam portion reflected from a surface without such a metallic backing layer. However, with a metallic backing layer, the absorption does show a wavelength dependence, so that it is difficult or impossible to ensure cancellation at the central point over a wide range of wavelengths. Furthermore when such a system is used in a Mach-Zehnder interferometer to approximate a circular pattern with a zero intensity center, the light at two orthogonal axes is plane polarized, which may result in incomplete quenching in a STED microscope, thereby reducing resolution. Furthermore such a solution is bulky, and to avoid loss of alignment with even small temperature changes requires operation in a very limited temperature range.

Thus there remains an unfulfilled need for apparatus to create zero central point patterns that is compact and accurate over a wide range of wavelengths without requiring readjustment.

OBJECTS AND ADVANTAGES

One object of the present invention is to provide a method of producing beams with an intensity distribution having a substantially zero intensity along the beam axis and/or in the beam focus, where the method allows the wavelength of the light to be changed without requiring any readjustment.

Another object of the present invention is to provide a method of producing beams with an intensity distribution having a substantially zero intensity along the beam axis and/or in the focus, where the beam has a broad spectral distribution.

Another object of the present invention is to provide a method of producing beams with an intensity distribution having a substantially zero intensity along the beam axis and/or in the focus which allows laser beams to be converted to such beam without requiring any beam expansion.

Another object of the present invention is to provide a method of producing beams with an intensity distribution having a substantially zero intensity along the beam axis and/or in the focus that consists of just transparent elements with parallel surfaces.

Another object of the present invention is to provide a device for producing beams with an intensity distribution having a substantially zero intensity along the beam axis and/or in the focus, that is sufficiently compact to be able to conveniently fit inside a microscope body, even, if necessary, close to the pupil plane of the objective lens.

SUMMARY OF THE INVENTION

A search is made for pairs of glass types that, at a particular thickness for each glass in the pair, the phase difference in propagation of light through one glass of the pair is exactly one half a wavelength relative to the other glass of the pair, for at least three different wavelengths spread out in the wavelength region of difference. Where one glass of the pair is called A and has a thickness TA and the other glass is B and has a thickness TB, eight squares of glass are made, two squares "A" of glass A of thickness TA, two squares "A*" of glass A of thickness TA/2, two squares "B" of glass B of thickness TB and two squares "B*" of glass B of thickness TB/2. Then four sandwiches of the squares are arrayed in a 2×2 quadrant square with a sandwich of glass A and A* in the upper left hand quadrant, of glass B and B* in the upper right hand quadrant, of glass B and A* in the lower right hand quadrant and of glass A and B* in the lower left hand quadrant. This array is then placed in the optical axis at either a pupil plane, a real image plane or an intermediate plane, and illuminated by a plane wave, perhaps having a Gaussian intensity profile. The light emerging from the array will have the desired properties of a zero intensity central axis and/or central point in an image plane, for the chosen wavelengths for which the half wavelength difference was exact, and close to a zero intensity for the intermediate wavelengths. This description describes several variations of this basic scheme.

BRIEF DESCRIPTION OF THE DRAWINGS

FIG. 3 is a three dimensional view of a phase retarding plate, tilted with respect to the axis of the incident laser beam, and where each of the eight component squares in the plate can be individually rotated to change the angle with respect to that optical axis so as to compensate for errors in the thickness of the plates.

FIG. 4 is a three-dimensional view showing a variation of the device shown in FIG. 3, in which two pairs of the plates have been merged into larger plates.

FIG. 5 is a three dimensional view showing how a pyramid made of triangular sheets of glass can redistribute the intensity distribution of the laser beam further from its axis, for possible improvements in brightness and sharpness of the resulting doughnut.

FIG. 6 is a schematic plan view showing how passage of the laser beam through the pyramid structure of FIG. 6 can redistribute the intensity distribution of the beam further from the axis.

DESCRIPTION OF THE INVENTION

Figure 1:
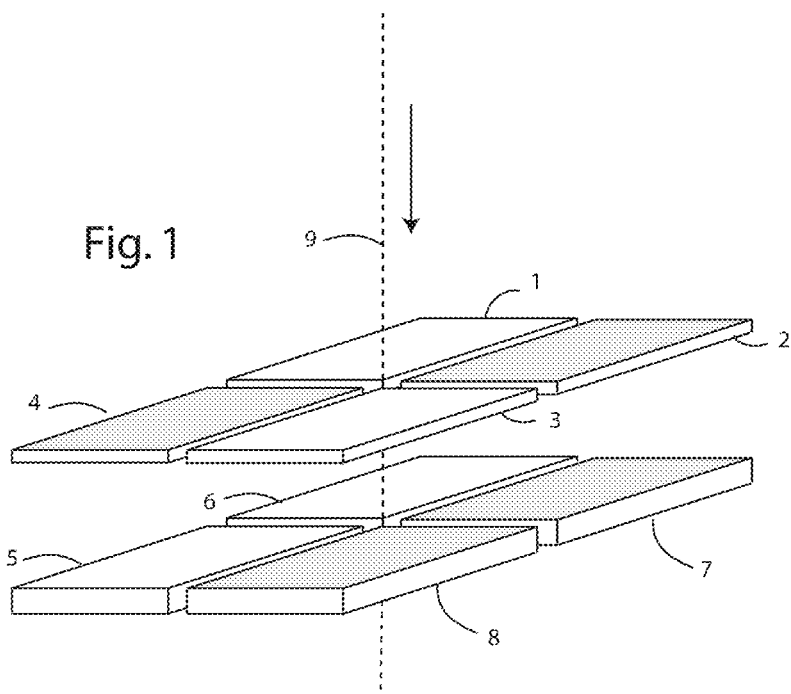
FIG. 1 is a three-dimensional view of a phase retarding plate according to the present invention.

FIG. 1 shows an exemplary embodiment of the present invention, in which elements 1 through 8 are glass sheets arranged in a sandwich of two 2×2 matrices, oriented normal to a laser beam 9 shown in the drawing by just its central ray. The direction of light in beam 9 is shown by an arrow. Sheets 1 and 3 are made of Sumita K-PMK10 glass of 82.503 µm in thickness. Sheets 2 and 4 are made of Schott N-PK51 glass of 82.286 µm in thickness. Sheets 5 and 6 are made of Sumita K-PMK10 glass of 165.005 µm in thickness. Sheets 7 and 8 are made of Schott N-PK51 glass of 164.571 µm in thickness.

Figure 2:
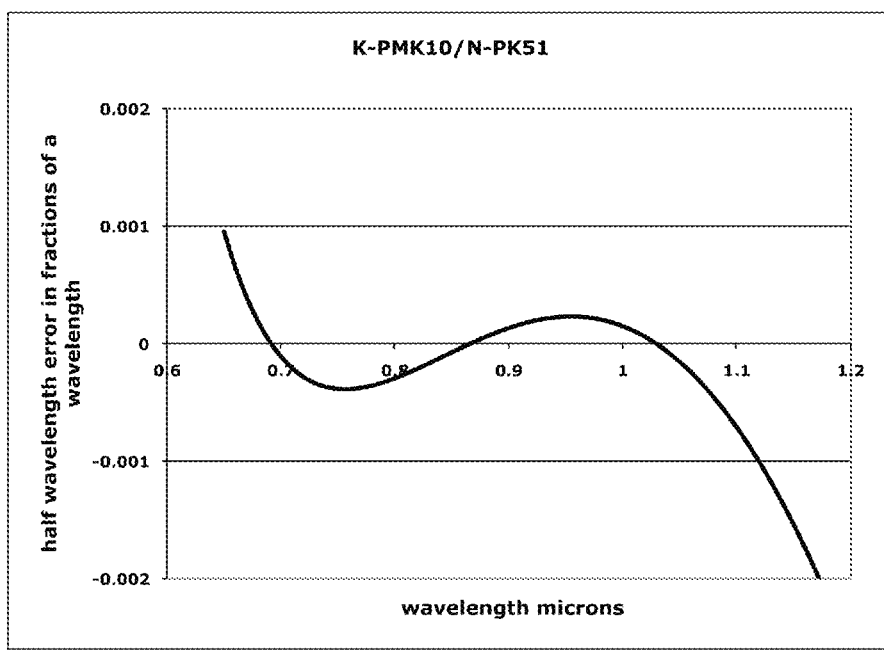
FIG. 2 is a graph showing the fractional deviation from a half wavelength relative phase retardation as a function of wavelength in a wave propagating through a sheet of Sumita K-PMK10 glass, 165.005 µm thick vs. a wave propagating through a sheet of Schott N-PK51 glass, 164.571 µm thick.

As will now be shown, over a large spectral range, light passing successively through sheets 1 and 6 is retarded almost exactly a half wavelength with respect to light passing successively through sheets 3 and 8. FIG. 2 shows a graph of the error as a fraction of a wavelength, plotted against wavelength, for the deviation from half wavelength relative retardation for two beams, one passing through a sheet, such as sheets 5 and 6 of Sumita K-PMK10 glass of 165.005 µm thick and the other passing through a sheet, such as sheets 7 and 8 of Schott N-PK51 glass of 164.571 µm thick. The curve shows that, over a spectral range from about 0.68 to 1.1 µm, the wavelength difference in the light from two beams which enter the plates in phase, will emerge with phase difference which is equal to a lambda/2 (half wavelength), within an error of less than about lambda/2000.

The laser beam 9 must pass through sheet 1 before passing through sheet 6, and must pass through sheet 3 before passing through sheet 8. Because sheets 1 and 3 are made of the same glass and have the same thickness, they will not contribute any phase difference to the light, so the phase difference is determined entirely by sheets 6 and 8, and therefore will correspond almost exactly to a half wavelength, over the spectral range from 0.68 to 1.1 µm. For the same reason, there is a half wavelength difference between the portion of beam 9 passing through sheets 5 and 7.

From the graph in FIG. 2, it will be clear to one skilled in the art, that if the two glass sheets had the same composition but half the thickness of the sheets measured in the graph, that the relative phase retardation would be a quarter rather than a half wavelength. Sheets 2 and 3 are such sheets, and therefore the relative phase retardation is a quarter wavelength. A portion of beam 9 passing successively through sheets 3 and 5 will be delayed a quarter of a wavelength with respect to a portion passing successively through sheets 2 and 7, because sheets 7 and 8, being identical, will contribute no phase difference, so any difference can be contributed only by sheets 2 and 3. By similar consideration it will be seen that in the sandwich of sheets shown in FIG. 1, when the spacing between the upper and lower sheets is small enough so that it is considered as a 2×2 matrix of smaller sandwiches, that diagonally opposite quadrants have a half wave retardation, that adjacent quadrants have a quarter wave retardation, and the relative phase is 0°, 90°, 180° and 270° moving clockwise around the matrix. This is the required phase retardation for four sources equally spaced around a common central point, to produce a doughnut-shaped beam, as described in Baer, U.S. Pat. No. 7,071,477, which is incorporated herein by reference. However, in the case of the four quadrant plate shown in FIG. 1, the plate is corrected almost exactly over the full range of the Titanium:Sapphire laser commonly used to form doughnut beams in STED microscopes. The device shown in FIG. 1, is completely corrected at the three wavelengths where the phase error is exactly zero, and is therefore apochromatic.

Although in the discussion, the thickness of the glass sheets has been specified to nanometer precision, there is some range where deviations from this specified thickness by one sheet could largely be compensated by a corresponding variation in the opposing sheet. This would permit a manufacturing operation, where sheets could be manufactured with, say, a 100 nm tolerance, but measured to a 1 nm tolerance, and matched to an appropriate opposing sheet.

To fabricate the plates to the indicated precision will require state of the art interferometric measurement combined with state of the art polishing apparatus, for example using a reactive atom plasma torch (Rapt Industries, Fremont, Calif.). In case thicker glass sheets are desirable to achieve the required precision in fabrication, or for ease of handling later, the thickness indicated can be multiplied times a small odd integer, and will still yield half and quarter wave relative delays.

FIG. 3 illustrates an arrangement of the plates shown in FIG. 1, where instead of being normal to the incident laser beam 9, the four-quadrant phase plate is tilted with respect to the beam. Because the tilting increases causes refraction at the plate surface, which increases the path length within the plate, it is necessary to decrease plate thickness to compensate for the tilting. The tilting of sheets 1, 2, 3 and 4 is on a common axis 10 and tilting of sheets 5, 6, 7 and 8 is on a common axis 11. One advantage with the tilting is that by tilting each individual member sheet within the array can individually adjust for deviations from the intended thickness. In the case of the arrangement in FIG. 1, tilting can only add effective thickness, not remove it, while with the arrangement in FIG. 3, tilting can both add and remove effective thickness. Many mechanisms for precise and stable tilting adjustment are known in the art. Hinges for tilting include leaf springs, knife edges and needle and cylindrical bearings. Adjustment of the angle could be with a screw, for example.

In the embodiment of the invention shown in FIG. 4, sheets 5 and 6 of FIG. 3 have been combined to form one sheet 15 and sheet 7 and 8 have been combined to form one sheet 16. This is possible both because the combined sheets are the made of the same glass and have the same thickness. Any variations in thickness between the two halves of sheet 15, for example, could be compensated by the tilting of sheet 1, and any variations in thickness of the two halves of sheet 16 could be compensated by the tilting of sheet 2. The ability to separately adjust the tilt of the 6 sheets in the apparatus of FIG. 4 allows full adjustment of the effective thickness of each sheet to optimum correction. And once adjusted, the adjustment will not have to be redone as the wavelength changes over the range of applicability, in this case from about 0.7 to 1.2 μm.

It should also be noted that in the apparatus in FIG. 4, the edges of the sheets that meet in the center are beveled to approximate vertical planes (more accurately, they are beveled to be parallel to the angle that a ray from beam 9 is refracted in the sheet). This allows the sheets to be closer to minimize the light from beam 9 passing between the sheets. Any residual light passing between the sheets is blocked by a cross shaped obstruction (unillustrated), since it would otherwise tend to increase the brightness of the central point of the doughnut-shaped pattern produced, which would have a deleterious effect in many applications.

As to the angle that the normal that the sandwich of 2×2 sheets in FIG. 4 makes with the axis of the laser beam 9, if the angle were around the Brewster angle of about 56°, it would be possible to avoid reflections without requiring any antireflective coating on the glass sheets. This would be desirable since antireflective coatings are a potential source of phase errors. However with a smaller angle, say about 10°, the effective thickness of the plate changes less with the angle, so it is easier to make small adjustments. Furthermore surface irregularities will less affect the path length. Finally, any reflections will be an angle that can be effectively absorbed by black surfaces in the instrument, and the loss of energy due to such reflections is relatively insignificant.

FIG. 5 shows the preferred embodiment of the present invention, in which a pyramid 20 is made of triangles of parallel-sided glass sheets, through which the laser beam 9 must traverse on its way to the sandwich of sheets. Pyramid 20 will refract four quadrants of beam 9 away from the axis, as shown by FIG. 6, which is a cross section through the pyramid, showing how two of its triangular plates 25 and 26, separately refract the portion of the beam 9 passing through them away from the axis. This separation is potentially beneficial because it allows the beam to avoid the area where the plates such as sheet 15 and sheet 16 meet, which without the pyramid would require masking to prevent transmission of the laser beam through that meeting area. Additionally, when beam 9 has a Gaussian distribution, such separation may increase both the intensity and the sharpness of the doughnut produced.

Figure 7:
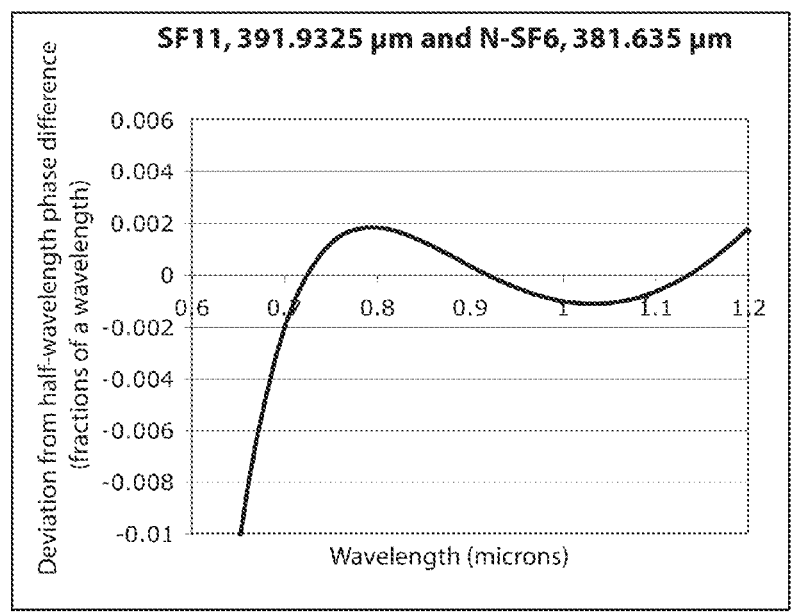
FIG. 7 is a graph showing the fractional deviation from a half wavelength relative phase retardation as a function of wavelength in a wave propagating through a different glass pair than shown in the graph in FIG. 2.

While the present invention has been described with respect to two specific glasses, there are other possible pairs of glass types which could also implement the present invention. For example FIG. 7 shows a curve for the deviation from half-wavelength phase difference for a ray passing normally through a sheet of Schott SF11 glass of 391.9325 μm thickness and a sheet of Schott N-SF6 glass of 381.635 μm thickness. It can be seen that the phase error is slightly less at the long wavelength end of the range between 0.6 and 1.2 μm, but is slightly greater at values on the intermediate and shorter wavelength parts of that range. Because the performance is very similar, other factors such as thermal coefficients of wavelength and expansion, ease of precision grinding and polishing thin sheets and availability would be part of the decision of which glass to use in a particular case. Other possible compatible pairs of glass, such as Schott N-BAK4 of 1,002.03 μm thickness and Schott N-SK2 of 9838.90 μm thickness are thicker than the first two pairs discussed, and might be used, specifically for the thinner set of sheets (1, 2, 3 and 4), which is should be noted, can be of different glasses those used for the thicker sheets (e.g., 15 and 16).

These examples of glass pairs were found in a search for glasses specifically for apparatus designed for the range of wavelengths now used in STED microscopy, and the range of the Titanium:Sapphire laser, though other pairs could be found for both a broader spectrum, or for a completely different range of the spectrum. The particular strategy for this search was 1) placing the all the different glasses in the Schott, Sumita, Hoya and Ohara catalogs in order of refractive index of the 852 nm cesium line, 2) for each pair of glasses separated by 43 positions or less on this ordered list, using the published refractive index at the 706.5 nm helium line and the 1014 nm mercury lines, finding the thickness of glass plates which will cause exactly a half wavelength propagation delay difference at these two lines, 3) using the calculated thickness at these wavelengths, and the refractive index at the 852 nm line, computing the error from half wavelength at the 852 nm line, a low error suggesting that the curve crosses the zero error line at three wavelengths in the desired spectral range, 4) for those glass pairs which both had a low error at 852 nm and also glass thickness that appeared practical for implementation of the present invention, computing the refractive index at 10 nm intervals, over the range from 600 nm to 1200 nm using the Sellmeier equation with published coefficients 5) with these refractive indices, calculating the error functions, such as shown in FIGS. 2 and 7, and 6) trying various perturbations of the thickness to optimize the error function.

Other search strategies are possible. The essential goal is to find glass pairs such that for each member of the pair, there is a thickness of a sheet, such that for three wavelengths spread out in a chosen wavelength range of application for the device, one generally near the blue end of the range, one generally close to the middle of the range, and the third generally close to the red end of the range, light passing normally through one of the sheets is delayed exactly a half wavelength with respect to light passing through the other sheet, and at all intermediate values the relative delay is close to a half-wavelength.

Figure 8:
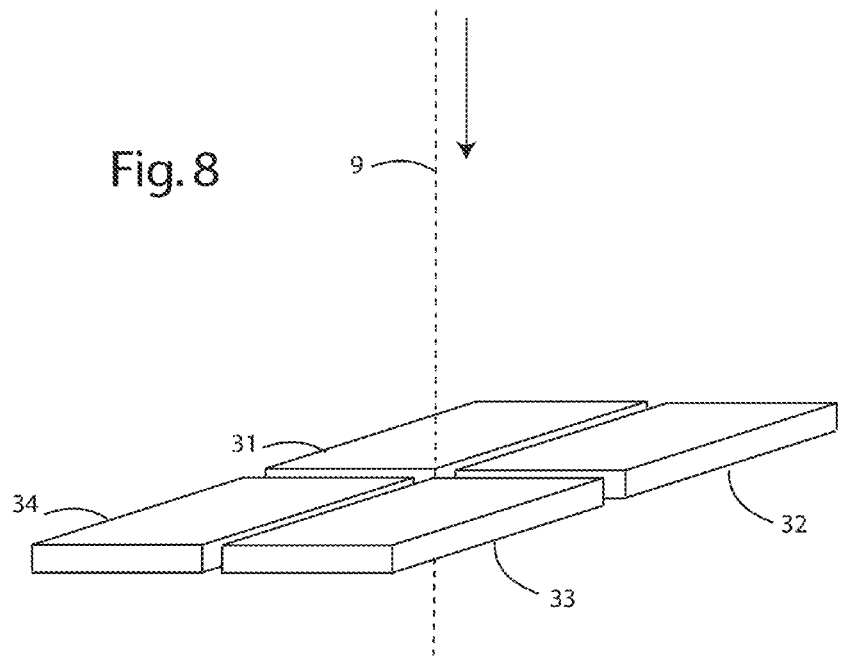
FIG. 8 is a three-dimensional view showing an embodiment of the present invention using four different types of glass, to allow the invention to be made with just four glass plates.

In the device of FIG. 8, the two-sheet sandwich of the device of FIG. 1 is replaced by a single sheet layer. This embodiment of the present invention would make assembly of the final product easier, and would eliminate two air/glass interfaces, per beam path for decreased spurious reflection, which should improve resolution. One way to implement the embodiment shown in FIG. 8 would be to laminate the sheet pairs, using various techniques known to make strong bonds between glass sheets without the use of any adhesive bonding layer, eg., described in Howlader et al, *Sensors and Actuators A: Physical*, 127:31 (06). Thus sheets 3 and 8 of FIG. 1 would be bonded together to form sheet 33 of FIG. 8, sheets 2 and 7 of FIG. 1 would be bonded to form sheet 32 of FIG. 8 etc.

Another way to implement the embodiment shown in FIG. 8 would be to find two pairs of glass compositions, such that each pair can yield an achromatic half wavelength difference when used for diagonal sheets, but the wavelength difference between adjacent sheets is a quarter wave. One possible such four glass combination would use as one pair of diagonally opposite sheets, eg., sheets 31 and 33, the same glasses and thicknesses illustrated in FIG. 1 (i.e., Sumita K-PMK10 glass, 165.005 μm thick and Schott N-PK51 glass, 164.571 μm thick.) A suitable glass pair for the remaining diagonally opposite sheets 32 and 34 would be, would be Schott N-PSK3 glass, 156.742 μm thick and Sumita G-FK68 146.635 μm thick. This particular four glass combination has a slightly greater error than the device shown in FIG. 1, but the error is low enough that it might not make any practical difference. And the convenience of having just one non-laminated plate per quadrant might balance a slight increase in error.

One additional four-glass composition, with greater error than the one already described, but possibly having other advantages, has as one opposite pair is N-SSK2, 259.23 μm thick and N-LAK10, 223.665 μm, and the other opposite pair is N-SK4, 263,352 μm thick and N-LAK9, 233.15 μm thick. The half-wavelength error from about 0.7 to 1.0 μm was less than about 0.005 wavelengths, while the adjacent pairs have a quarter-wavelength error between pairs of less than about 0.02 wavelengths over the same spectral range.

Figure 9:
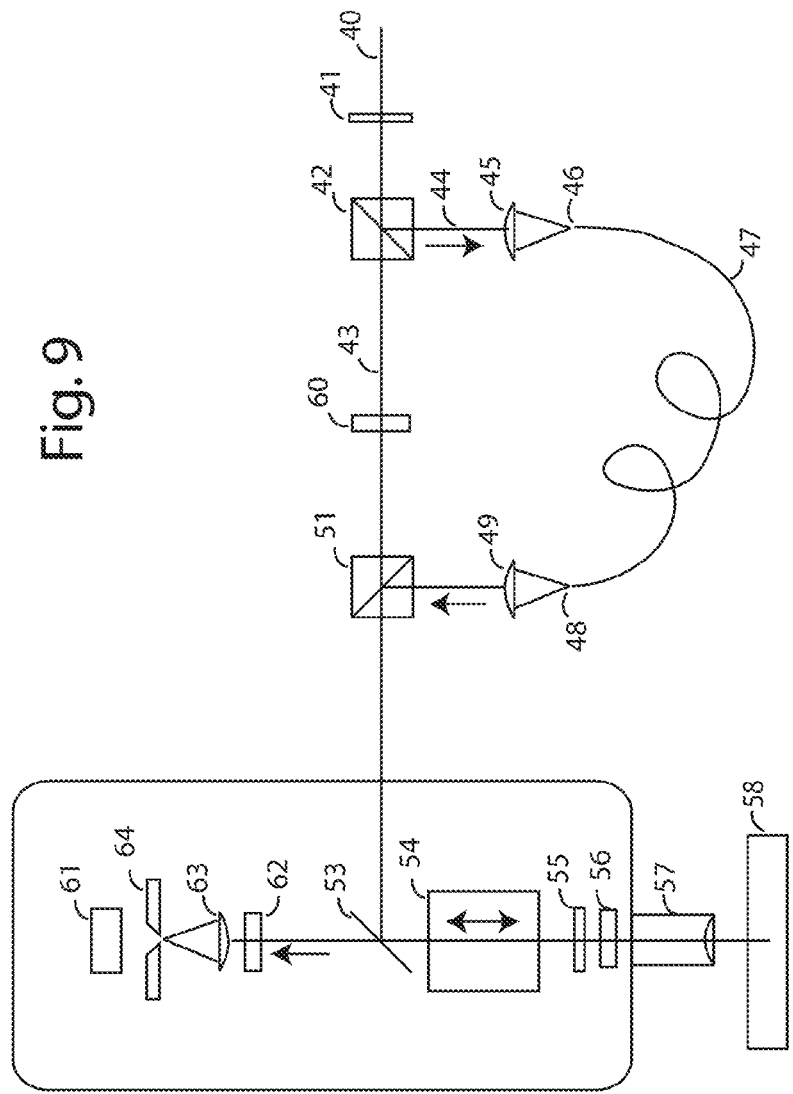
FIG. 9 is a schematic plan view showing a single wavelength STED microscope that utilizes the present invention.

The utility of the present invention is illustrated particularly in the Single Wavelength STED microscope apparatus shown in FIG. 9, which is an improvement of the devices disclosed in Baer, PCT US 06/01961, the entire disclosure of which is incorporated herein by reference. All prior art STED microscopes having the capacity to create zero-center doughnut patterns have included means for converting an incoming laser beam, usually with a Gaussian profile, into a beam with a zero intensity axial ray, and/or a substantially zero-centered doughnut pattern in the focal plane of the specimen. Every optical element between such converting means and the objective lens of the microscope is a potential source of wavefront distortion, scattering and spurious reflections that can lower the quality of the imaged doughnut-shaped pattern. For that reason, the ideal location of such converting means is directly adjacent to the objective lens thereby eliminating those intervening optical elements. However none of these prior art STED microscopes have specified such a location adjacent to the objective, partly because the converting means was bulky and inconvenient to fit into the small space near the objective in an existing microscope body and required access to adjust for changes in wavelength. Furthermore, in a location adjacent to the objective lens, such converting means would change the excitation beam into a doughnut as well as the quenching beam, and the doughnut beam should be a spot rather than a doughnut.

The device in FIG. 9 shows how use of the present invention as the means to produce a zero-centered beam overcomes these problems when such means is located adjacent to the objective lens. Laser beam 40, from a Titanium:Sapphire laser, consisting of a train of pulses of duration on the order of 100 fs, and a frequency on the order of 100 MHz, passes through a rotatable half-wave plate 41 on its way to polarizing beam splitter 42, which transmits the minor fraction of the beam power as beam 43. Beam 43 will ultimately become focused to form the excitation spot. Beam splitter 42 reflects a major fraction of the incoming beam power as beam 44, which will become the doughnut-shaped quenching beam, the precise division of power between beams 43 and 44 being determined by the rotation of half-wave plate 41. Beam 44 is focused by lens 45 onto one end 46 of a long optical fiber 47, which by introducing group-velocity dispersion, stretches the pulse to the order of 200 ps or longer. (Additional unillustrated elements, such as a parallel-sided block of glass, may be included between lens 45 and end 46 to pre-stretch the pulse to reduce damage in fiber 47.) The stretched pulse leaving end 48 of fiber 47 is recollimated by lens 49, and the resulting collimated beam 50 is directed to polarizing beam splitter 51 which reflects nearly 100% of beam 50 to the microscope body where it is reflected by dichroic beam splitter 53 through the scanner and intermediate optics in box 54, and then through a quarter-wave plate 55 to convert the plane polarized light to circularly polarized. This circularly polarized light in a collimated beam is then passed through the four-quadrant device 56 of the present invention, converting it to a zero intensity axis beam, which the objective 57 then focuses to a doughnut-shaped pattern at the focal plane of specimen 58.

Ensuring that the scanning means, such as galvanometer minors (unillustrated) within box 54 limit the angle with respect to the optical axis, to an angle small enough so as not to disturb the relative retardation of the sheets of device 56 will remain accurate, then scanning can be provided by such means, and the doughnut will be scanned in a raster pattern over the chosen focal area of specimen 58 by means of scanners in box 54. The highest amplitude scan would be possible in such case, when four quadrant plate 56 were of the type shown in FIGS. 1 and 8, where the surface of the sheets is normal to the optical axis, since with such orientation, small angle deviations from the normal will make a minimal change in path length through the sheets. In case the scan angle disturbs the relative retardation, then scanning can be provided by lateral translation of the objective 57 and or the specimen 58, or possibly both, with translation of the objective producing high frequency line scanning and translation of the specimen producing the lower frequency frame scanning Still another method of scanning would be to have a vibrating minor scanner provide a very low amplitude line scan for a narrow strip, which is scanned in the orthogonal direction by a slower movement of the objective. A still slower movement of the specimen relative to the objective moves the area of the scanned strips over the desired field of the specimen. In this way, the angular movement of the beam relative to four-quadrant plate 56 can be held to within limits that do not affect its phase retardation calibration, and but at the same time, the movement of elements close to the specimen can be relatively slow.

That portion of beam 40 which is transmitted by polarizing beam splitter 42 to form beam 43 is directed through a second four-quadrant plate 60 of the present invention, similar to four-quadrant plate 56, but where the phase change is in the opposite direction (as if plate 56 were turned upside down). Plate 60 may be in a plane conjugate to plate 56 (from imaging of plate 56 onto plate 60 by relay lens optics in box 54 and at other, unillustrated places in the ray paths), so that each of the sheets in plate 60 is imaged on a corresponding sheet in plate 56. Any relative phase changes due plate 60 are, as best as possible, cancelled by passage through plate 56, so that beam 43 is focused to a spot in specimen 58, such that the central maximum point of the spot coincides with the zero point of the doughnut-shaped beam. It should be noted that passage through the two plates 60 and 56 may not exactly cancel the phase retardations, and as such the focused spot of excitation light may be of larger diameter than if plates 60 and 56 were not in the path. However because in the STED microscope, resolution is determined by the half-width of the central minimum of the doughnut shaped beam, such imperfections in the formation of the excitation spot will not affect resolution.

Fluorescent light emitted from the excited spot in the specimen, following quenching by the doughnut shaped beam, is focused by objective 57 onto light detector 61, after passing in succession through four-quadrant plate 56, quarter wave plate 55, box 54, dichroic beam splitter 53 (which transmits the light), a third four-quadrant plate 62, which may be conjugate to plate 56, so as to cancel any relative phase differences imparted by plate 56, lens 63 and confocal pinhole 64, which is at the focus of the beam focused by lens 63. The electrical signal from detector 61, by synchronization with the scanning movements of the excitation spot relative to the specimen, leads to the formation of an image, by means well known in the art of laser scanning microscopy.

The wide spectral correction of the four quadrant plate 56 is particularly important in the device of FIG. 9 because not only does it have to be corrected at the wavelengths of the excitation and quenching beams, but it also must be corrected for the intrinsically broad band spectrum of the fluorescent emission. Furthermore the fact that the four quadrant plate of the present invention is compact and does not require any adjustment after its initial calibration leads itself to the device of FIG. 9, where the three four-quadrant plates can be imbedded into the optical system, without requiring constant access.

Figure 10:
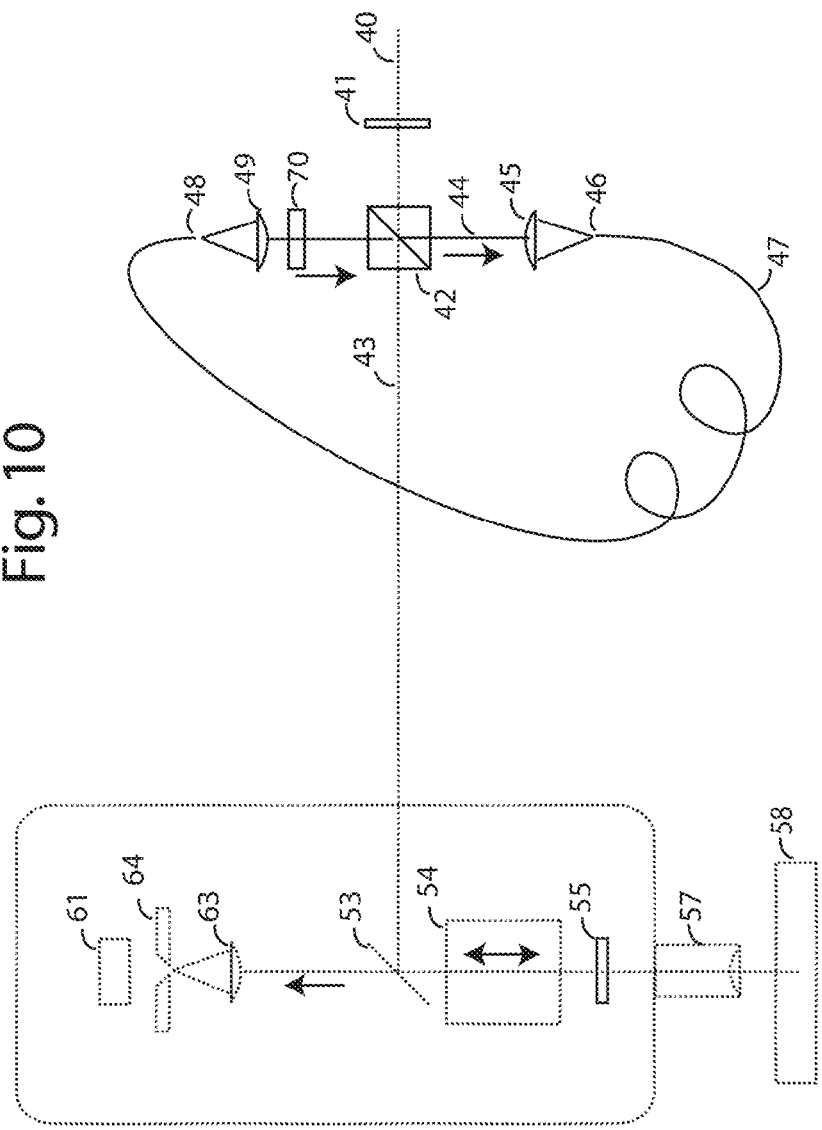
FIG. 10 is a schematic plan view showing a second example of a STED microscope that utilizes the present invention.

Use of the four-quadrant plate of the present invention is illustrated in a second example of Single Wavelength STED microscope in FIG. 10, where the design goal was to produce a STED microscope of maximum simplicity and minimum cost. All the elements that have the same function as in the microscope of FIG. 9 have been labeled as in FIG. 9, and the function will not be described further here. It will be seen that the single polarizing beam splitter 42 functions both in its original role as shown in FIG. 9, but also in the role of beam splitter 51 of FIG. 9. This both eliminates the need for an optical element, but reduces by half, the length of glass traversed by the excitation beam, and therefore requires less compensation for group-velocity dispersion to maintain the minimum pulse width of that beam. The microscope of FIG. 10 contains just one four-quadrant plate 70 located between the recollimating lens 49 and beam splitter 42. Plate 70 may be in a pupil plane of the microscope. Because the axis of the light incident on plate 70 does not change with scanning, such scanning may be by rotating mirrors in box 54, and plate 70 need not be normal to the optical axis, facilitating adjustment of the thickness of its individual sheets. The components in the microscope of FIG. 10 already on a multiphoton microscope have been shown with dotted lines, to emphasize how few components have to be added to such a microscope to convert it into a STED microscope.

The microscope of FIG. 10 is expected to produce a doughnut-shaped pattern that has more residual brightness of the central point than the pattern produced by the device of FIG. 9, because additional optical elements intervene between the four-quadrant plate and the objective. However because the superior wavelength correction of the four-quadrant plate it is expected that the microscope would produce images that match or exceed those of any other state of the art STED microscope.

The embodiments of the invention described so far have produced just one zero center beam or doughnut, however it is possible with well known means, for example involving lens arrays, to generate arrays of doughnut shaped patterns, from the output of the beam produced by the above described apparatus, and these arrays could be useful for microscopes which employ parallel data collection to reduce the frame time, or reduce the exposure time for photolithographic embodiments of the invention. An alternative way of generating arrays of doughnut shaped patterns is by focusing an array of retarding elements onto the focal plane of the specimen, such as the array shown in FIG. 17 of U.S. Pat. No. 7,071,477, the entire contents of which is incorporated herein by reference. Each of the circles in the diagram could be replace by a small (e.g., millimeter square) plate of according to the formula described in this description, to create a tile pattern.

The forgoing description has specified that the sheets be made of glass, however they could be made of other transparent materials. Although the examples in the description considered the beam passing through four quadrants, it is possible to imagine alternative embodiments of the invention with different numbers of sectors, where opposite sectors have a half wave phase difference, but where the phase difference between adjacent sectors decreases as the number of sectors increases. The examples given showed the application of the present invention to STED microscopy, yet there are other forms of high resolution microscope using doughnut shaped beams, and the present invention could improve those methods as well. Additionally the resolution enhancement provided by the present improvement to the production of zero-centered beams could be applied in the field of microlithography, nanofabrication, high density data storage, optical tweezers manipulation of small particles and acceleration and focusing of electrons. Furthermore the description specified that the radiation supplied by laser 9 was light, however other sources of radiation, for which there is need to shape the radiation into a doughnut shaped beam, and where the radiation has a range of wavelengths, could be substituted for the light in the present description. Thus scope of the present invention should be understood by the claims rather than by these particular examples.

The invention claimed is:

1. A device for shaping a light beam to have an intensity distribution having at least one point of substantially zero intensity, said device having a beam axis, the device comprising a plurality of transparent plates of varying thickness, wherein said plates are disposed substantially in a plane, so that said plates are arrayed in relation to said axis, so that different portions of said beam pass through different transparent plates, wherein a first transparent plate has a first composition and wherein a second transparent plate has a second composition different from the first composition of the first transparent plate, and wherein said compositions and thicknesses of said plates are chosen such that at any wavelength in a wavelength range of at least several tens of nanometers said beam portions experience particular phase delays in passing through their corresponding plates, such that said particular phase delays cause said beam portions to interfere at said at least one point to produce a substantially zero intensity.

2. The device of claim 1, wherein said first transparent plate and said second transparent plate are on opposite sides of said axis and wherein the beam portions transmitted through said first and second plates have a phase difference of half the wavelength of the light of said beam portions, causing the light to interfere on said axis, producing substantially zero intensity on said axis.

3. The device of claim 2 wherein said axis, having a substantially zero intensity, passes through a focal point which therefore also has a substantially zero intensity.

4. The device of claim 1 wherein at least one of said plates comprises a sandwich of two sheets.

5. The device of claim 1, wherein said compositions and thicknesses of said plates are chosen such that a first beam portion passing through a first plate and directed to said at least one point and a second beam portion passing through a second plate and directed to said at least one point experience a phase difference of lambda/n, where lambda is a wavelength in said wavelength range of the light of said beam portions and n is a small integer.

6. The device of claim 1, wherein said compositions and thicknesses of said plates are chosen such that at any wavelength in a wavelength range of at least 100 nm said beam portions experience particular phase delays in passing through their corresponding plates, such that said particular phase delays cause said transmitted beam portions to interfere at said at least one point to produce a substantially zero intensity.

7. The device of claim 1, wherein said compositions and thicknesses of said plates are chosen such that at any wavelength in a wavelength range of at least 400 nm said beam portions experience particular phase delays in passing through their corresponding plates, such that said particular phase delays cause said transmitted beam portions to interfere at said at least one point to produce a substantially zero intensity.

8. A method for shaping a light beam, having a beam axis, to have an intensity, distribution having at least one point of substantially zero intensity comprising the steps:
providing a plurality of transparent plates of varying thickness, disposing said plates substantially in a plane, directing said beam on said plane,
arraying said plates in relation to said axis, so that different portions of said beam pass through different transparent plates, wherein a first transparent plate has a first composition and wherein a second transparent plate has a second composition different from the first composition of the first transparent plate, and
choosing said compositions and thicknesses of said plates such that at any wavelength in a wavelength range of at least several tens of nanometers said beam portions experience particular phase delays in passing through their corresponding plates, such that said particular phase delays cause said beam portions after passing though their corresponding plates to interfere at said at least one point to produce a substantially zero intensity.

9. The method of claim 8, wherein said compositions and thicknesses of said plates are chosen such that, in said wavelength range, for a first wavelength near the short wavelength end of said range, for a second wavelength near the long wavelength end of said range, and for a third wavelength between those first and second wavelengths, the phase difference of the beam portions after passing through their corresponding plates is exactly half the wavelength of the transmitted beam portions.

10. The method of claim 8, wherein said first transparent plate and said second transparent plate are on opposite sides of said axis and wherein the beam portions after passing through said first and second plates have a phase different of half the wavelength of the light of said beam portions, causing the light to interfere at said at least one point, producing zero intensity at said point.

11. The method of claim 8, wherein said at least one point is on said axis, and is a focal point.

12. The method of claim 8, wherein at least one of said plates comprises a sandwich of two sheets.

13. The method of claim 8, wherein said compositions and thicknesses of said plates are chosen such that a first beam portion passing through a first plate and directed on said at least one point and a second beam portion passing through a second plate and directed on said at least one point experience a phase difference of lambda/n, where lambda is a wavelength of the light of said beam portions and n is a small integer.

14. The method of claim 8, wherein said compositions and thicknesses of said plates are chosen such that at any wavelength in a wavelength range of at least 100 nm said beam portions experience particular phase delays in passing through their corresponding plates, such that said particular phase delays cause said transmitted beam portions to interfere at said at least one point to produce a substantially zero intensity.

15. The method of claim 8, wherein said compositions and thicknesses of said plates are chosen such that at any wavelength in a wavelength range of at least 400 nm said beam portions experience particular phase delays in passing through their corresponding plates, such that said particular phase delays cause said transmitted beam portions to interfere at said at least one point to produce a substantially zero intensity.

* * * * *